United States Patent [19]

Batch et al.

[11] 4,230,484

[45] Oct. 28, 1980

[54] CONTROL OF POLLEN FORMATION

[75] Inventors: Jeremy J. Batch, Sunninghill; Keith P. Parry, Maidenhead; Colin F. Rowe, Slough; David K. Lawrence, Reading, all of England; Michael J. Brown, Randolph Township, Morris County, N.J.

[73] Assignee: Imperial Chemical Industries Limited, London, England

[21] Appl. No.: 900,007

[22] Filed: Apr. 25, 1978

[30] Foreign Application Priority Data

May 5, 1977 [GB] United Kingdom ............... 18862/77

[51] Int. Cl.$^3$ ............................................. A01N 37/44
[52] U.S. Cl. ........................................ 71/111; 71/98;
71/100; 71/105; 71/115; 260/455 A; 260/465
D; 560/9; 560/24; 560/26; 560/27; 560/29;
560/30; 560/33; 560/75; 560/102; 560/105;
560/109; 560/111; 560/112
[58] Field of Search .............................. 71/111; 560/43

[56] References Cited

U.S. PATENT DOCUMENTS

| 3,317,584 | 5/1967 | Stoffel | 560/43 |
| 3,511,804 | 5/1970 | Duennenberger et al. | 560/43 |
| 3,901,684 | 8/1975 | Lin | 71/111 |
| 4,018,813 | 4/1977 | Gaughan | 71/111 |
| 4,069,343 | 1/1978 | Sellstedt et al. | 560/43 |

FOREIGN PATENT DOCUMENTS

| 2273523 | 1/1976 | France | 560/43 |
| 1170115 | 11/1969 | United Kingdom | 560/43 |
| 1449934 | 9/1976 | United Kingdom | 560/43 |
| 1514775 | 6/1978 | United Kingdom | 560/43 |

OTHER PUBLICATIONS

Takeda, "Plant Growth Regulants Compositions, etc.," (1969), Derw. Jap. Pat. Rept., vol. 8, No. H7013 (1969).
Toatsu, "Chloroanilide Ders. Nematocides", (1971), Derw. Jap. Pat. Rept., vol. S, No. 50823S-C (1971).
Baruffini et al., "Oxanilic Acid Ders.", (1967), CA 68 No. 77924V (1968) and Farmaco Ed. Sci. 22, pp. 717–734, (1967).
Sellstedt et al., "Oxanilic Acids, a New Series etc.," (1975), J. Med. Chem. 18, pp. 926–933, (1975).

Primary Examiner—Glennon H. Hollrah
Attorney, Agent, or Firm—Cushman, Darby & Cushman

[57] ABSTRACT

A method of controlling pollen formation in a hermaphrodite plant, the method comprising applying to the plant, to seed of the plant or to the locus surrounding the plant or seed, a compound of formula:

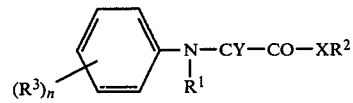

wherein $R^1$ is hydrogen or alkyl, $R^2$ is hydrogen, alkyl, alkyl substituted with up to three halogens (e.g. trichloro- or trifluoro-methyl), cycloalkyl, alkoxyalkyl (e.g. 2-methoxy-ethyl), substituted or unsubstituted aryl or aralkyl or an alkali metal (e.g. sodium or potassium), alkaline earth metal or quaternary ammonium cation, $R^3$ is halogen, nitro, alkyl, alkyl substituted with up to three halogens (e.g. trichloro- or trifluoro-methyl), cycloalkyl, alkoxy, alkylthio, amino, acylamino (e.g. acetylamino), mono- or di-alkylamino, acyl (e.g. acetyl), haloacyl (e.g. bromoacetyl), cyano, amido, hydroxy, carboxy, alkoxycarbonyl (e.g. methoxycarbonyl) or phenoxy, n is 0 or an integer of 1 to 5 (preferably 0, 1, 2 or 3) and each of X and Y, which may be the same or different, is oxygen or sulphur.

1 Claim, No Drawings

CONTROL OF POLLEN FORMATION

This invention relates to a method of controlling pollen formation in monoecious and hermaphrodite plants using oxanilates and their derivatives. The control of pollen formation generally involves killing the gametes, i.e. the agents used in the pollen control have gametocidal activity. The invention also relates to certain of the oxanilates and their derivatives themselves.

Monoecious palnts are plants wherein the male and female inflorescences are separate but are carried by the same plant. Examples of monoecious plants are maize, cucumber and hemp.

It is sometimes desirable to control the pollination of monoecious plants. A monoecious plants in which pollen control is most desirable is maize because the varieties grown commercially are generally F1 hybrids. In maize, hybrids are generally hardier than pure strains in maize and further they give a better yield of product. The formation of such hybrids can be illustrated by the cross-pollination of strain AA with strain BB to give hybrid AB. In maize, the male inflorescence is the apex (or tassel) while the female inflorescence is the cob (or ear). To obtain F1 hybrids, it is customary to plant strips of AA maize adjacent to strips of BB maize. The tassels of the AA maize are removed by hand or by machine or alternatively special sterile strains of AA maize are employed. In both cases, the AA maize is cross-pollinated with BB maize to give AB maize. However, neither of these techniques is wholly satisfactory and it would be desirable to achieve satisfactory cross-pollination to give AB hybrids by ensuring that the AA maize does not produce any pollen.

Hermaphrodite plants are plants wherein the male and female organs are in the same flower. In the self-pollinating species, the female ovule is pollinated by the male pollen in the same flower while in the cross-pollinating species the pollen fertilises ovules in different flowers. Examples of such hermaphrodite plants are wheat and barley. It is sometimes desirable to control the formation of pollen in such plants. As with the monoecious plants, this is generally done because it is desired to produce hybrids. Hybrids are usually hardier than pure strains and further in cereal plants they can in some circumstances give a better yield of grain. Thus it is desirable to inhibit the development of pollen in plants such as barley in order to facilitate cross-pollination and hybridisation with untreated barley varieties present in the same field.

We have found that certain oxanilates and their derivatives have a pollen controlling activity in certain plants.

The invention therefore provides a method of controlling pollen formation in a monoecious or hermaphrodite plant, the method comprising applying to the plant, to seed of the plant or to the locus surrounding the plant or seed, a compound of general formula (I):

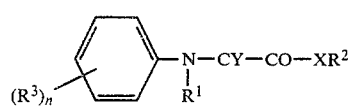

wherein $R^1$ is hydrogen or alkyl, $R^2$ is hydrogen, alkyl, alkyl substituted with up to three halogens (e.g. trichloro- or trifluoro-methyl), cycloalkyl, alkoxyalkyl (e.g. 2-methoxyethyl), substituted or unsubstituted aryl or aralkyl or an alkali metal (e.g. sodium or potassium), alkaline earth metal or quaternary ammonium cation, $R^3$ is halogen, nitro, alkyl, alkyl substituted with up to three halogens (e.g. trichloro- or trifluoro-methyl), cycloalkyl, alkoxy, alkylthio, amino, acylamino (e.g. acetylamino), mono- or di-alkylamino, acyl (e.g. acetyl), haloacyl (e.g. bromoacetyl), cyano, amido, hydroxy, carboxy, alkoxycarbonyl (e.g. methoxycarbonyl) or phenoxy, n is 0 or an integer of 1 to 5 (preferably 0, 1, 2 or 3) and each of X and Y, which may be the same or different, is oxygen or sulphur.

When n is greater than 1, the groups $R^3$ can be the same or different.

The alkyl and alkoxy groups suitably have 1 to 5 carbon atoms; they can be straight or branched chain groups. Examples are methyl, ethyl, propyl, (n- or i-propyl), butyl (n-, i- or t- butyl), methoxy or ethoxy. The cycloalkyl groups suitably have 3 to 6 carbon atoms; examples are cyclopropyl, cyclopentyl and cyclohexyl.

A suitable halogen is fluorine, chlorine, bromine or iodine.

When $R^2$ is aryl, it is suitably phenyl and when $R^2$ is aralkyl, it is suitable benzyl or phenylethyl. These groups can be ring-substituted with for example up to three substituents selected from the class consisting of halogen, alkyl [e.g. methyl, ethyl, propyl, (n- or i- propyl) and butyl (e.g. n-, i- or t-butyl)], nitro, trifluoromethyl, cyano, alkoxy (e.g. methoxy or ethoxy), phenyl and alkylenedioxy (e.g. methylenedioxy). The benzyl (and other aralkyl) groups can also be substituted on their alkyl moieties; examples of suitable substituents are alkyl and phenyl.

A preferred class of compounds are those wherein the

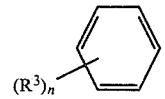

group is phenyl itself, 2-, 3- or 4-fluorophenyl, 2-, 3- or 4-chlorophenyl, 2-, 3- or 4-bromophenyl, 2-, 3- or 4-iodophenyl, 2,3-, 3,4- or 2,4-dichlorophenyl, 2,4,5- or 2,4,6-trichlorophenyl, 2,4,6-tribromophenyl, 2-, 3- or 4-methoxyphenyl, 3,5-dimethoxyphenyl, 2,5-diethyoxyphenyl, 2-, 3- or 4-methylthiophenyl, 2-, 3- or 4-tolyl, 2,3- or 3,4-dimethylphenyl, 2,4,5-trimethylphenyl, 2-, 3- or 4-ethylphenyl, 2-, 3- or 4-acetylphenyl, 3-bromoacetyl, 2-, 3- or 4-aminophenyl, 2-, 3- or 4-nitrophenyl, 2-, 3- or 4-trifluoromethyl phenyl, 3,5-di(trifluoromethyl)-phenyl, 2-amidophenyl, 2-carboxyphenyl, 2-methoxycarbonylphenyl, 2-hydroxyphenyl, 4-acetylaminophenyl, 2-, 3- or 4-cyanophenyl, 4-dimethylaminophenyl, 3-diethylaminophenyl, 4-cyclopropylphenyl, 4-phenoxyphenyl, 2-chloro-4-iodophenyl, 2-chloro-4-bromophenyl, 3-chloro-4-fluorophenyl, 2-nitro-4-chlorophenyl, 3-nitro-4-fluorophenyl, 2-methyl-4-fluorophenyl, 2-methyl-5-fluorophenyl, 3-fluoro-4-methylphenyl, 3-methyl-4-bromophenyl, 3-methyl-4-chlorophenyl, 2-methyl-4-chlorophenyl, 2-methyl-5-chlorophenyl, 4-cyano-2,3,5,6-tetrafluorophenyl, 3-trifluoromethyl-4-chlorophenyl, 3-trifluoromethyl-4-bromophenyl, 2-bromo-5-trifluoromethylphenyl or 2-methoxy-5-acetylaminophenyl; $XR^2$ is hydroxy, methoxy, ethoxy, i-propoxy, n-propylthio, i-propylthio, t-butoxy, cyclohexyloxy, 2-methoxyethyoxy, benzyloxy or 2-phenylethoxy; $R^1$ is hydrogen or methyl; and Y is oxygen or sulphur.

Examples of suitable compounds of general formula (I) are shown in Table I.

TABLE I

| Compound No. | $R^1$ | $XR^2$ | $(R^3)_n$ | Y | Melting (or Boiling) Point (°C.) |
|---|---|---|---|---|---|
| 1 | H | OH | 4-NH$_2$ | O | |
| 2 | H | OEt | 3-CH$_3$CO | O | |
| 3 | H | OEt | 4-Cl | O | 151°–154° |
| 4 | H | OEt | 2-NO$_2$-4-Cl | O | |
| 5 | H | OEt | 3-NH$_2$ | O | |
| 6 | H | OEt | 4-MeO | O | 112°–114° |
| 7 | H | OEt | H | O | |
| 8 | H | OEt | 3-Cl | O | |
| 9 | H | OMe | H | O | |
| 10 | H | OMe | 2-CONH$_2$ | O | |
| 11 | H | OMe | 2-COOMe | O | |
| 12 | H | OEt | 3,5-diMeO | O | 107° |
| 13 | H | OEt | 2,5-diEtO | O | 86° |
| 14 | H | OEt | 3-CF$_3$ | O | 122° |
| 15 | H | OEt | 2-MeO | O | |
| 16 | Me | OEt | H | O | |
| 17 | H | OEt | 4-Me | O | |
| 18 | H | OH | H | O | |
| 19 | H | OEt | 4-NO$_2$ | O | |
| 20 | H | OEt | 4-F | O | 118.5° |
| 21 | H | OEt | 2-COOH | O | |
| 22 | H | OEt | 3-NO$_2$ | O | |
| 23 | H | OEt | 3-BrCH$_2$CO | O | |
| 24 | H | OEt | 3,4-diCl | O | |
| 25 | H | OEt | 3-Me | O | 58.5° |
| 26 | H | OEt | 2,3-diMe | O | |
| 27 | H | OEt | 3-MeS | O | |
| 28 | H | OEt | 2-NO$_2$ | O | |
| 29 | H | OEt | 3,5-diCF$_3$ | O | 87°–90° |
| 30 | H | OEt | 4-Et | O | 55°–58° |
| 31 | H | OEt | 3-Et | O | 36°–40° |
| 32 | H | OEt | 2,4,5-triMe | O | 77°–78° |
| 33 | H | OEt | 2,3-diCl | O | 73°–76° |
| 34 | H | OEt | 2-F | O | |
| 35 | H | OEt | 2,4-diCl | O | 119°–120° |
| 36 | H | OEt | 2-Cl-4-Br | O | 116°–117° |
| 37 | H | OEt | 4-CF$_3$ | O | 137°–142° |
| 38 | H | OEt | 4-Br | O | 152°–153° |
| 39 | H | OEt | 4-I | O | 146°–147° |
| 40 | H | OEt | 3-Cl-4-F | O | 130°–131° |
| 41 | H | OEt | 2-I | O | oily solid |
| 42 | H | OEt | 2-Me-4-F | O | 98°–99° |
| 43 | H | OEt | 2-Me-5-F | O | oil |
| 44 | H | OEt | 3-F-4-Me | O | 93°–94° |
| 45 | H | OEt | 3-Me-4-Br | O | 133°–134° |
| 46 | H | OEt | 2-Cl-4-I | O | 128°–129° |
| 47 | H | OEt | 3-NO$_2$-4-F | O | 121°–122° |
| 48 | H | OEt | 2-SMe | O | |
| 49 | H | OEt | 3-CF$_3$-4-Cl | O | 130°–135° |
| 50 | H | OEt | 3-CF$_3$-4-Br | O | |
| 51 | H | OEt | 2-OMe-5-CH$_3$CONH | O | |
| 52 | H | OEt | 2,4,6-triBr | O | |
| 53 | H | OEt | 2-Me-4-Cl | O | 94°–97° |
| 54 | H | OEt | 3-Me-4-Cl | O | 97°–100° |
| 55 | H | OEt | 2,4,5-triCl | O | 99°–104° |
| 56 | H | OEt | 2-Cl | O | (122°–127°/0.6mm) |
| 57 | H | OEt | 2-Me-5-Cl | O | 70°–73° |
| 58 | Me | OEt | 2-Cl | O | |
| 59 | Me | OEt | 2-NO$_2$ | O | |
| 60 | H | OEt | 4-F | S | 61°–63° |
| 61 | H | OEt | 4-CN-2,3,5,6-tetraF | O | 111°–112° |
| 62 | H | OEt | 2-Br-5-CF$_3$ | O | |
| 63 | H | S-n-Pr | 4-F | O | 82° |
| 64 | H | S-n-Pr | 2-Me-4-F | O | |
| 65 | H | S-n-Pr | 4-I | O | |
| 66 | H | S-n-Pr | 4-Cl | O | 160°–162° |
| 67 | H | OEt | 4-NMe$_2$ | O | 114°–117° |
| 68 | H | OEt | 3,4-diMe | O | 68°–71° |
| 69 | H | S-n-Pr | 2,4-diCl | O | 66°–68° |
| 70 | H | S-n-Pr | 3-Me-4-Br | O | |
| 71 | H | OEt | 4-cyclopropyl | O | 89°–90° |
| 72 | H | S-n-Pr | 2-MeO | O | |
| 73 | H | OEt | 3-F | O | 83°–88° |
| 74 | H | OEt | 3-I | O | 150°–155° |
| 75 | H | OEt | 3-Br | O | 126°–132° |
| 76 | H | OEt | 2-Me | O | (133°–134°/0.6mm) |
| 77 | H | OEt | 2-Br | O | (132°–134°/0.9mm) |
| 78 | H | OEt | H | S | |
| 79 | H | OEt | 4-Cl | S | 99°–101° |
| 80 | H | OEt | 4-Me | S | 80°–83° |
| 81 | H | OEt | 4-MeO | S | |
| 82 | H | OEt | 3,4-diMe | S | 63°–66° |
| 83 | H | OEt | 4-CF$_3$ | S | 97°–100° |
| 84 | H | OEt | 4-Me$_2$N | S | |
| 85 | H | OEt | 3-Cl | S | |
| 86 | H | OEt | 3-CF$_3$-4-Cl | S | |
| 87 | H | OEt | 3,4-diCl | S | |
| 88 | H | OEt | 3-CN | O | 144° |
| 89 | H | OEt | 4-CN | O | 189° |
| 90 | H | OH | 4-CF$_3$ | O | 185°–186° |
| 91 | H | OEt | 4-PhO | O | 104° |
| 92 | H | OH | 4-Cl | O | 189°–190° (dec) |
| 93 | H | OH | 4-F | O | 144°–145° (dec) |
| 94 | H | O-i-Pr | 4-Cl | O | 137° |
| 95 | H | OMe | 4-Cl | O | 162° |
| 96 | H | OMe | 4-CF$_3$ | O | 190° |
| 97 | H | OMe | 4-F | O | 156° |
| 98 | H | O-cyclohexyl | 4-F | O | 117° |
| 99 | H | O-cyclohexyl | 4-Cl | O | 155°–158° |
| 100 | H | O(CH$_2$)$_2$Ph | 4-Cl | O | 162° |
| 101 | H | OCH$_2$Ph | 4-CF$_3$ | O | 112° |
| 102 | H | OCH$_2$Ph | 4-Cl | O | 125° |
| 103 | H | O(CH$_2$)$_2$Ph | 3-Cl | O | 95° |
| 104 | H | O-cyclohexyl | 4-CF$_3$ | O | 136° |
| 105 | H | S-i-Pr | 4-CF$_3$ | O | 114° |
| 106 | H | OEt | 4-CH$_3$CO | O | 146° |
| 107 | H | OEt | 4-MeS | O | 139.5° |
| 108 | H | OEt | 2-CN | O | 89° |
| 109 | H | OEt | 4-CH$_3$CONH | O | 195° |
| 110 | H | O-t-Bu | 4-Cl | O | 134.5° |
| 111 | H | OCH$_2$Ph | 4-F | O | 96°– |

TABLE I-continued

| Compound No. | $R^1$ | $XR^2$ | $(R^3)_n$ | Y | Melting (or Boiling) Point (°C.) |
|---|---|---|---|---|---|
| 112 | H | O(CH$_2$)$_2$Ph | 4-CF$_3$ | O | 104° 128°–129° |
| 113 | H | O(CH$_2$)$_2$Ph | 4-F | O | 123° |
| 114 | H | O-t-Bu | 4-CF$_3$ | O | 135° |
| 115 | H | O-t-Bu | 4-F | O | 130.5° |
| 116 | H | O(CH$_2$)$_2$OMe | 4-Cl | O | 120° |
| 117 | H | O(CH$_2$)$_2$OMe | 4-F | O | 113° |
| 118 | H | O(CH$_2$)$_2$OMe | 4-CF$_3$ | O | 120°–121° |
| 119 | H | OEt | 2-OH | O | >250° |
| 120 | Me | OEt | 4-Cl | O | (142°/0.94 mm) |
| 121 | Me | OEt | 4-F | O | (125–127°/0.97 mm) |
| 122 | Me | OEt | 4-CF$_3$ | O | |
| 123 | H | OEt | 3-Et$_2$N | O | |

"dec" means "with decomposition".

The compounds of general formula (I) wherein Y is oxygen can be prepared by reacting a compound of general formula (II):

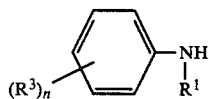

(II)

wherein $R^1$, $R^3$ and n are as defined above, or an acid addition salt thereof, with a compound of general formula (III):

 (III)

wherein Z is halogen, alkoxy or alkylthio.

When a compound of general formula (I) wherein X and Y are both oxygen is required, the compound of general formula (III) is suitably an oxalic acid mono- or di-ester (for example an oxalic acid dialkyl ester e.g. diethyl oxalate) or oxalyl monohalide monoester (for example an alkyl or aralkyl oxalyl halide e.g. ethyl oxalyl chloride).

While the reaction with diethyl oxalate can be performed by merely heating the reactants together, it is preferred to heat them in a solvent (e.g. toluene) in the presence of, as catalyst, boric acid (in for example an amount of 0.01 mole). The solvent should be one which does not react with the reactants; for this reason the use of ethyl acetate is not recommended. The use of higher boiling solvents (e.g. toluene) improves the rate of reaction.

The reaction with ethyl oxalyl chloride is the preferred way of preparing these compounds. It is suitably performed by mixing the reactants under cooling in the presence of a solvent (e.g. ethyl acetate) in the presence of a base such as triethylamine.

The compounds of general formula (I) wherein Y is oxygen and X is sulphur are best prepared using a compound of general formula (III) wherein $XR^2$ and Z are both alkylthio (e.g. ethylthio). This reaction is suitably performed by heating the reactants in a solvent such as toluene.

To prepare the compounds of general formula (I) wherein Y is sulphur, the corresponding compound of general formula (I) wherein Y is oxygen can be sulphurated. The sulphuration is suitably performed using phosphorus pentasulphide as the sulphurating agent and in the presence of a solvent such as toluene.

The compounds wherein $XR^2$ is hydroxy can be obtained by hydrolysing the corresponding ester, e.g. alkyl ester, using for example methanolic hydrochloric acid.

The compounds of general formula (II) wherein $R^1$ is alkyl can be prepared by heating under acidic conditions a compound of general formula (IV)

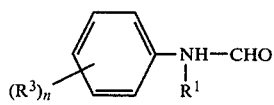

(IV)

wherein $R^3$ and n are as defined above and $R^1$ is alkyl.

The product of the above reactions can be isolated in known manner.

To achieve pollen control, the compounds are preferably applied in the form of compositions, in which the active ingredient is mixed with a diluent or carrier. The compounds may be applied for uptake by the plant either by bringing them directly into contact with plant foliage (e.g. by spraying) or by introducing them into the soil in which the roots of the plant grow, e.g. as a dressing on seeds.

The compositions may be in the form of dusting powders or granules comprising the active ingredients and a solid diluent or carrier, for example fillers such as kaolin, bentonite, kieselguhr, dolomite, calcium carbonate, talc, powdered magnesia, Fuller's earth, gypsum, Hewitt's earth, diatomaceous earth and China clay. Such granules can be preformed granules suitable for application to the soil without further treatment. These granules can be made either by impregnating pellets of filler with the active ingredient or by pelleting a mixture of the active ingredient and powdered filler. Compositions for dressing seed, for example, may comprise an agent (for example a mineral oil) for assisting the adhesion of the composition to the seed; alternatively the active ingredient can be formulated for seed dressing purposes using an organic solvent (for example N-methylpyrrolidone or dimethylformamide).

The compositions may also be in the form of dispersible powders, granules or grains comprising a wetting agent to facilitate the dispersion in liquids of the powder or grains which may contain also fillers and suspending agents.

The aqueous dispersions or emulsions may be prepared by dissolving the active ingredient(s) in an organic solvent optionally containing wetting, dispersing or emulsifying agent(s) and then adding the mixture to water which may also contain wetting, dispersing or emulsifying agent(s). Suitable organic solvents are ethylene dichloride, isopropyl alcohol, propylene glycol, diacetone alcohol, toluene, kerosene, methylnaphthalene, the xylenes, trichloroethylene, furfuryl alcohol, tetrahydrofurfuryl alcohol, and glycol ethers (e.g. 2-ethoxyethanol and 2-butoxyethanol).

The compositions to be used as sprays may also be in the form of aerosols wherein the formulation is held in a container under pressure in the presence of a propellant, e.g. fluorotrichloromethane or dichlorodifluoromethane.

The compounds can be mixed in the dry state with a pyrotechnic mixture to form a composition suitable for generating in enclosed spaces a smoke containing the compounds.

Alternatively, the compounds may be used in a microencapsulated form. Microcapsules may be made by co-acervation, or, more preferably, by stirred interfacial polymerisation of an isocyanate/dianine system. The microcapsules may be used as an aqueous suspension.

By including suitable additives, for example additives for improving the distribution, adhesive power and resistance to rain on treated surfaces, the different compositions can be better adapted for various utilities.

The compositions may also be in the form of liquid preparations for use as dips or sprays which are generally aqueous dispersions or emulsions containing the active ingredient in the presence of one or more surfactants e.g. wetting agent(s), dispersing agent(s), emulsifying agent(s) or suspending agent(s). These agents can be cationic, anionic or non-ionic agents. Suitable cationic agents are quaternary ammonium compounds, for example cetyltrimethylammonium bromide.

Suitable anionic agents are soaps, salts of aliphatic monoesters of sulphuric acid (for example sodium lauryl sulphate), and salts of sulphonated aromatic compounds (for example sodium dodecylbenzenesulphonate, sodium, calcium or ammonium lignosulphonate, butyl-naphthalene sulphonate, and a mixture of sodium diisopropyl- and triisopropyl-naphthalene sulphonates).

Suitable non-ionic agents are the condensation products of ethylene oxide with fatty alcohols such as oleyl or cetyl alcohol, or with alkyl phenols such as octyl- or nonylphenol and octylcresol. Other non-ionic agents are the partial esters derived from long chain fatty acids and hexitol anhydrides, the condensation products of the said partial esters with ethylene oxide, and the lecithins. Suitable suspending agents are hydrophilic colloids (for example polyvinylpyrrolidone and sodium carboxymethylcellulose), and the vegetable gums (for example gum acacia and gum tragacanth).

The compositions for use as aqueous dispersions or emulsions are generally supplied in the form of a concentrate containing a high proportion of the active ingredient(s), the concentrate to be diluted with water before use. These concentrates often should be able to withstand storage for prolonged periods and after such storage be capable of dilution with water in order to form aqueous preparations which remain homogeneous for a sufficient time to enable them to be applied by conventional spray equipment. The concentrates may conveniently contain up to 95%, suitably 10–85%, for example 25–60%, by weight of the active ingredient(s). After dilution to form aqueous preparations, such preparations may contain varying amounts of the active ingredient(s) depending upon the intended purpose, but an aqueous preparation containing 0.01% to 10%, preferably 0.01% to 1%, by weight of active ingredient(s) may be used.

The compositions of this invention can comprise also other plant growth regulating agents.

If desired, the compositions may contain other plant growth regulating agents.

When pollen control in maize is performed, the tassel of the maize is often completely killed, or at least made sterile; in addition sometimes cob development is enhanced. This enhancement manifests itself in earlier silking, larger cobs and/or more cobs per plant.

Most compounds capable of controlling pollen formation only show the pollen control effect at a specific stage in the development of the plant. They tend to cause phytotoxicity in the plant when applied at a slightly earlier stage. They also tend to cause phytotoxicity when applied at slightly higher concentrations that that at which the pollen control effect is noticed, even where the compound is applied at the correct stage in development for pollen control activity. Thus a good pollen control compound should have as wide as possible stage in development wherein the pollen control effect is observed, a good safety margin between this stage and the phytotoxic stage and a similar safety margin with respect to the rate of application.

The precise stage of development and application rate for a particular plant must usually be established by experimentation, but in general the compounds show pollen control activity in maize in the glasshouse at 25–5000, preferably 50–4000 and especially 250 or 500–2000, p.p.m. The compounds are preferably applied during the second half of the period from sowing to tassel emergence and preferably around the time of meiosis. Suitable stages are Stages 4 to 7 as disclosed in "Growth Stages of Maize/Corn" from the U.S. Department of Agriculture, Technical Bulletin 976, and from Hanway, Spec. Rep. 48 of the Iowa State University, 1966, the disclosure of which document is incorporated herein by reference.

However allowance must be taken of the fact that the phytotoxic effect will almost certainly be observed at some stage in development of the plant. Application made significantly later than that at which the pollen control effect is noticed may be ineffective. Thus uneven results could be obtained in the field since it is inevitable that there will be plants at varying stages of development in the field. The use of granules or other formulations which slowly release the active compounds in the soil can often be used to overcome this problem.

Similarly with barley, the precise stage of development and application rate for a particular plant must usually be established by experimentation, but in general the compounds show pollen control activity on barley at a rate of 100 to 10000, preferably 600 to 6000, p.p.m. in the glasshouse (rates in the field may differ significantly from this range), and at around the time of meiosis. Meiosis occurs before the ears and anthers emerge.

In some monoecious plants (e.g. those of the cucurbit family e.g. cucumber), the male and female flowers are not grouped into separate male and female inflorescences; instead they are borne singly throughout the plants. In such plants, only the female flowers contribute to the production of a useful product and it would be desirable if the numbers of female flowers were increased. The compounds of general formula (I) may be able to do this by reversing the sex of the male flowers. The compounds are generally applied at an early growth stage.

The invention is illustrated by the following Examples, wherein the temperatures are given in degrees centigrade (°C.).

EXAMPLE 1

Diethyloxalate (133 g) and p-fluoroaniline (100 g) were refluxed together for 2 hours, during which time the temperature dropped from 160° to 100°. The dark coloured mixture (with suspended crystalline solid) so produced was allowed to cool to 90°, and then diluted with ethanol (100 ml). After cooling overnight, the crystalline product was filtered off and washed thoroughly with cyclohexane. The white solid so obtained, was thoroughly dried to give ethyl 4'-fluorooxanilate (114 g; 60% yield), m.p. 117°–119° (with softening at 116°).

EXAMPLE 2

Ethyl p-fluorooxanilate and phosphorus pentasulphide (4 g) in toluene (100 ml) were refluxed for 24 hours to give a bright orange mixture. The mixture was filtered and washed with water (3×100 ml) and dried ($Na_2SO_4$) and the solvent evaporated in vacuo. The product (an orange oil) was dissolved in diethyl ether and filtered to remove traces of insoluble material. The product was too soluble in all organic solvents (e.g. ethanol and chloroform) tried for recrystallisation. On standing overnight in the absence of a solvent, the oil crystallised to bright orange crystals which were dissolved in the minimum volume of petroleum ether (40°–60°) and left in a stoppered flask for 3 days. White crystals formed in the bottom of the flask. After standing for a further 7 days, the solution was filtered and the solvent evaporated to give, as fluffy orange crystals, ethyl 4'-fluoro-2-thionooxanilate (1.2 g), m.p. 61°–63°.

EXAMPLE 3

Dipropyl dithioloxalate (2.2 g) and p-fluoroaniline (1.1 g) in toluene (20 ml) were brought to reflux. After 15 minutes, a white solid precipitated. The reaction mixture was heated for a further 15 minutes and then the solid was filtered off. Recrystallisation from acetone gave, as white crystals, S-n-propyl 4'-fluoro-thiolooxanilate (2.3 g; 90yield) m.p. 82°.

EXAMPLE 4

4-Amino benzotrifluoride (5 g) in chloroform (25 ml) was added slowly to ethyl oxalyl chloride (4.2 g) in the presence of triethylamine (3.1 g; 4.3 ml) in chloroform (100 ml) keeping the temperature below 10°. The mixture was allowed to warm to room temperature and was then stirred for 2 hours. It was washed with water (3×100 ml), dried ($MgSO_4$) and filtered, and the solvent evaporated to give a buff solid (8.05 g). The solid was recrystallised from ethyl acetate/petroleum ether (60°–80°). The slightly yellow crystals were filtered off. The crystals (3.81 g) were taken up in ethyl acetate and refluxed with activated charcoal and filtered; the solvent was evaporated off to give a pale yellow solid which was recrystallised from ethyl acetate/petroleum ether (60°–80°) to give, as a white solid, ethyl 4'-trifluoromethyloxanilate (3.0 g); m.p. 137°–142°.

EXAMPLE 5

The pollen controlling activity of the compounds on barley was determined as follows.

The test compound was applied to barley (variety Mari) at a rate of 5,000 ppm a.i. and in the form of a solution (20 ml) sprayed to run-off on 3 replicate pots each containing 4 plants. The compound was applied in the primary tests at a stage of development close to meiosis in the oldest florets of the main shoot. The secondary testing was performed at several stages before and after this 'meiotic' stage.

Grain setting is used as an estimate of gametocidal activity—absence of grain or reductions in grain number indicating high and low levels of activity, respectively.

The pollen control activity was assessed according to the following scale:
O: inactive
+: slightly active
++: moderately active
+++: highly active
The compounds had the following activities:
O = Compounds 12, 13, 17, 34, 40, 41, 42, 45, 46, 50, 71.
+ = Compounds 1, 2, 4, 11, 14, 23, 25, 27, 28, 30, 35, 36, 39, 43, 44, 47, 48, 49, 51, 52, 53, 54, 55, 56, 59, 61, 64, 67, 70, 72, 76, 77, 81, 84, 85, 86, 87, 92, 93, 106, 109.
++ = Compounds 5, 6, 8, 9, 10, 15, 16, 18, 19, 21, 22, 24, 31, 33, 57, 58, 62, 65, 68, 69, 73, 74, 75, 78, 80, 99, 100, 102, 103, 105, 107, 111, 113, 121, 122.
+++ = Compounds 3, 7, 20, 26, 29, 37, 38, 60, 63, 66, 79, 83, 88, 89, 90, 91, 94, 95, 96, 97, 98, 101, 104, 108, 110, 112, 114, 115, 116, 117, 118, 119, 120.

EXAMPLE 6

The compounds were tested for their pollen control activity on maize. The test compound was sprayed onto the maize plants (variety "First of All") at meiosis or about 1 week before meiosis. 30 Ml of a solution of the test compound was applied at a rate of 4000 p.p.m. to plants in each of three replicate pots each containing 1 plant. Observations were made on the tassel only for the following pollen control effects: sex reversal, death or structural immaturity of the tassel, delay in tassel emergence, exertion of the anthers and shedding of pollen. The pollen control activity was assessed according to the following scale:
O: inactive
+: slightly active
++: moderately active
+++: highly active
The compounds had the following activities:
O = Compounds 6, 8, 14, 17, 24, 35, 36, 38, 39, 40, 44, 53, 55, 64, 65, 67, 68, 69, 70, 72, 73, 75, 76, 77, 80, 83.
+ = Compounds 3, 4, 7, 34, 37, 43, 46, 49, 50, 51, 56, 63, 66, 71, 74.
++ = Compounds 20, 41, 42, 45.
+++ = Compound 60.

We claim:
1. A method of controlling pollen formation in hermaphrodite plants, the method consisting essentially of the step of applying to the plant at or around the time of meiosis in the plant a pollen controlling amount of a compound of formula:

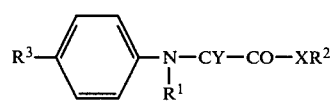

wherein $R^1$ is hydrogen, X and Y are both oxygen, $R^2$ is ethyl and $R^3$ is trifluoromethyl.

* * * * *